United States Patent [19]

Eicken et al.

[11] Patent Number: 5,591,747
[45] Date of Patent: Jan. 7, 1997

[54] FUNGICIDAL MIXTURES

[75] Inventors: Karl Eicken, Wachenheim; Bernd Müller, Frankenthal; Hubert Sauter, Mannheim; Gisela Lorenz, Neustadt; Eberhard Ammermann, Heppenheim; Klaus Schelberger, Gönnheim; Reinhold Saur, Böhl-Iggelheim, all of Germany

[73] Assignee: BASF Aktiengesellschaft, Ludwigshafen, Germany

[21] Appl. No.: 550,540

[22] Filed: Oct. 30, 1995

Related U.S. Application Data

[62] Division of Ser. No. 305,396, Sep. 13, 1994, Pat. No. 5,508,283.

[30] Foreign Application Priority Data

Sep. 13, 1993 [DE] Germany ............ 43 30 970.4

[51] Int. Cl.⁶ ............ A01N 37/18; A01N 43/54
[52] U.S. Cl. ............ 514/275; 514/619
[58] Field of Search ............ 514/275, 619

[56] References Cited

U.S. PATENT DOCUMENTS 5,373,013  12/1994  Hubele et al. ............ 514/275
5,395,854  3/1995  Brand et al. ............ 514/619

*Primary Examiner*—Allen J. Robinson
*Attorney, Agent, or Firm*—Oblon, Spivak, McClelland, Maier & Neustadt, P.C.

[57] ABSTRACT

A fungicidal synergistic mixture containing
a) a compound of the formula I

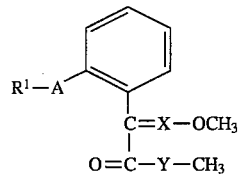

where the substituents have the following meanings:

$R^1$ is a phenyl radical which can carry one to three of the following groups: cyano, halogen, $C_1$–$C_4$-alkyl, $C_1$–$C_2$-haloalkyl and $C_1$–$C_4$-alkoxy, or a pyrimidyl radical which can carry a $C_1$–$C_3$-alkyl group and/or a phenoxy group, the phenoxy group in turn being able to carry one to three of the following radicals: cyano, halogen, $C_1$–$C_4$-alkyl, $C_1$–$C_2$-haloalkyl and $C_1$–$C_4$-alkoxy, A is oxygen or oxymethylene (—$OCH_2$—);

X is CH or N,

Y is oxygen or $NR^2$, $R^2$ being hydrogen, $C_1$–$C_3$-alkyl or $C_1$–$C_3$-alkoxy, and b) a pyrimidine derivative of the formula II

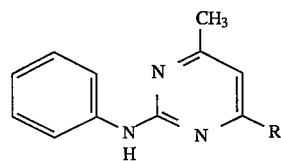

where R is methyl, propyn-1-yl or cyclopropyl, in a synergistically active amount, is described.

6 Claims, No Drawings

FUNGICIDAL MIXTURES

This is a Division of application Ser. No. 08/305,396 filed on Sep. 13, 1994, now U.S. Pat. No. 5,508,283.

The present invention relates to a fungicidal mixture which contains a) a compound of the formula I

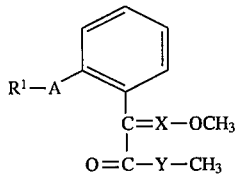

where the substituents have the following meanings:

$R^1$ is a phenyl radical which can carry one to three of the following groups: cyano, halogen, $C_1$–$C_4$-alkyl, $C_1$–$C_2$-haloalkyl and $C_1$–$C_4$-alkoxy, or a pyrimidyl radical which can carry a $C_1$–$C_3$-alkyl group and/or a phenoxy group, the phenoxy group in turn being able to carry one to three of the following radicals: cyano, halogen, $C_1$–$C_4$-alkyl, $C_1$–$C_2$-haloalkyl and $C_1$–$C_4$-alkoxy, A is oxygen or oxymethylene (—$OCH_2$—);

X is CH or N,

Y is oxygen or $NR^2$, $R^2$ being hydrogen, $C_1$–$C_3$-alkyl or $C_1$–$C_3$-alkoxy, and b) a pyrimidine derivative of the formula II

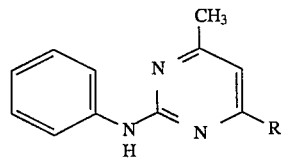

where R is methyl, propyn-1-yl or cyclopropyl, in a synergistically active amount.

The invention additionally relates to processes for combating harmful fungi using the compounds I and II and synergistic mixtures containing them and to the use of the compounds I or the compounds II for the production of mixtures of this type. Compounds of the formula I, their preparation and their action against harmful fungi are disclosed in the literature (EP-A 253 213, EP-A 382 375, EP-A 398 692).

The pyrimidine derivatives II, their preparation and their action against harmful fungi are likewise known [R=methyl: DD-A 151 404 (common name: pyrimethanil); R=1-propynyl: EP-A 224 339 (common name: mepanipyrim); R=cyclopropyl: EP-A 310 550].

With respect to a decrease in the application rates and an improvement in the spectrum of action of the known compounds, the present invention is based on mixtures which, with a decreased total amount of applied active compounds, have an improved action against harmful fungi (synergistic mixtures).

Accordingly, the mixtures defined at the beginning have now been found. It has additionally been found that, with simultaneous joint or separate application of the compounds I and the compounds II or with application of the compounds I and the compounds II successively, harmful fungi can be combated better than with only the compounds I or II.

With respect to the C=X double bond, the compounds of the formula I can be present in the E configuration or the Z configuration (with respect to the groups $OCH_3$ and CO—$YCH_3$). Accordingly, they can be used in the mixture according to the invention either as pure isomers or as an E/Z isomer mixture. Preferably, the E/Z isomer mixture or the E isomer is used, in many cases the E isomer being particularly preferred.

Because of the basic character of the NH group, the pyrimidine derivatives of the formula II are able to form salts with inorganic or organic acids or with metal ions.

Examples of inorganic acids are hydrohalic acids such as hydrofluoric acid, hydrochloric acid, hydrobromic acid and hydriodic acid, sulfuric acid, phosphoric acid and nitric acid.

Suitable organic acids are, for example, formic acid, carbonic acid and alkanoic acids such as acetic acid, trifluoroacetic acid, trichloroacetic acid and propionic acid as well as glycolic acid, thiocyanic acid, lactic acid, succinic acid, citric acid, benzoic acid, cinnamic acid, oxalic acid, alkylsulfonic acids (sulfonic acids with straight-chain or branched alkyl radicals having 1 to 20 carbon atoms), arylsulfonic acids or -disulfonic acids (aromatic radicals such as phenyl and naphthyl which carry one or two sulfonic acid groups), alkylphosphonic acids (phosphonic acids with straight-chain or branched alkyl radicals having 1 to 20 carbon atoms), arylphosphonic acids or -diphosphonic acids (aromatic radicals such as phenyl and naphthyl which carry one or two phosphoric acid radicals), the alkyl or aryl radicals being able to carry further substituents, eg. p-toluenesulfonic acid, salicylic acid, p-aminosalicylic acid, 2-phenoxybenzoic acid, 2-acetoxybenzoic acid etc.

Suitable metal ions are in particular the ions of the elements of the second main group, in particular calcium and magnesium, of the third and fourth main group, in particular aluminum, tin and lead, and of the first to eighth sub-group, in particular chromium, manganese, iron, cobalt, nickel, copper, zinc and others. The metal ions of the elements of the sub-groups of the fourth period are particularly preferred. The metals in this case can be present in the different valencies applicable to them.

Preferably, for the provision of the fungicidal mixtures according to the invention, compounds I are used where the substituents have the following meanings:

$R^1$ is a phenyl radical which can carry one to three of the following groups: cyano, halogen, $C_1$–$C_2$-alkyl, $C_1$–$C_2$-haloalkyl and $C_1$–$C_2$-alkoxy, or a pyrimidyl radical which can carry a $C_1$–$C_2$-alkyl group and/or a phenoxy group, the phenoxy group in turn being able to carry one to three of the following radicals: cyano, halogen, $C_1$–$C_2$-alkyl, $C_1$–$C_2$-haloalkyl and $C_1$–$C_2$-alkoxyl, A is oxygen or oxymethylene (—$OCH_2$—);

X is CH or N,

Y is oxygen or $NR^2$, $R^2$ being hydrogen, $C_1$–$C_2$-alkyl or $C_1$–$C_2$-alkoxy.

Particularly preferred fungicidal mixtures are those which contain compounds I where the substituents have the following meanings:

$R^1$ is a phenyl radical which can carry one to three of the following groups: halogen, methyl, trifluoromethyl and methoxy, A is oxymethylene (—$OCH_2$—), X is CH or N, Y is oxygen or $NR^2$, $R^2$ being hydrogen, methyl or methoxy.

Particularly preferred fungicidal mixtures are also those which contain compounds I where the substituents have the following meanings:

$R^1$ is a pyrimidyl radical, in particular a pyrimidine-4,6-diyl radical, which can carry a methyl group and/or a phenoxy group, the phenoxy group in turn being able to carry one to three of the following radicals: cyano, halogen, methyl, trifluoromethyl and methoxy, A is oxygen;

X is CH or N,

Y is oxygen or $NR^2$ $R^2$ being hydrogen, methyl or methoxy

Particularly preferred mixtures are additionally those which contain a compound of the formula I where $R^1$ is 2-methylphenyl or 2,5-dimethylphenyl, A is oxymethylene, X is N and Y is oxygen or NH.

In addition mixtures are preferred which contain a compound of the formula I where $R^1$ is 2-methylphenyl or 2,5-dimethylphenyl, A is oxymethylene, X is N and Y is NH.

Additionally mixtures are preferred which contain a compound of the formula I where $R^1$ is 6-{2-cyanophenoxy}pyrimidin-4-yl, A is oxygen, X is CH and Y is oxygen.

With respect to utility as mixture components the compounds I.A, I.B and I.C are particularly preferred.

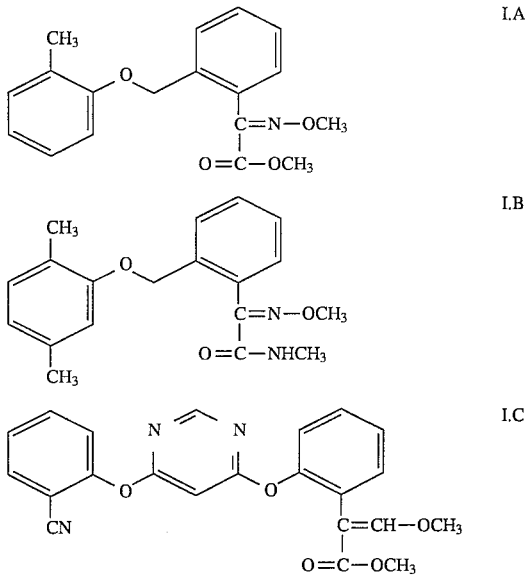

Preferably, in the preparation of the mixtures the pure active compounds I and II are employed, to which, if needed, further active compounds against harmful fungi or other pests such as insects, arachnids or nematodes, or alternatively herbicidal or growth-regulating active compounds or fertilizers, can be admixed.

The mixtures of the compounds I and II and the simultaneous joint or separate use of the compounds I and II are distinguished by an outstanding action against a wide spectrum of phytopathogenic fungi, in particular from the Ascomycetes and Basidiomycetes class. In some cases they are systemically active and can therefore also be employed as foliar and soil fungicides.

They have particular importance for combating a multiplicity of fungi on various crop plants such as cotton, vegetable plants (eg. cucumbers, beans and cucurbits), barley, grass, oats, coffee, maize, fruit plants, rice, rye, soybean, grape, wheat, decorative plants, sugar cane and a multiplicity of seeds.

In particular, they are suitable for combating the following phytopathogenic fungi: *Erysiphe graminis* (powdery mildew) on cereals, *Erysiphe cichoracearum* and *Sphaerotheca fuliginea* on cucurbits, *Podosphaera leucotricha* on apples, Puccinia species on cereals, Rhizoctonia species on cotton and lawns, Ustilago species on cereals and sugar cane, *Venturia inaequalis* (scab) on apples, Helminthosporium species on cereals, *Septoria nodorum* on wheat, *Botrytis cinera* (gray mold) on strawberries and vines, *Cercospora arachidicola* on groundnuts, *Pseudocercosporella herpotrichoides* on wheat and barley, *Pyricularia oryzae* on rice, *Phytophthora infestans* on potatoes and tomatoes, *Plasmopara viticola* on vines, Alternaria species on vegetables and fruit and also Fusarium and Verticillium species.

They can additionally be used in material protection (eg. wood preservation), for example against *Paecilomyces variotii*.

The compounds I and II can be applied simultaneously jointly or separately or successively, the sequence when applied separately in general having no effect on the combating success.

The compounds I and II are customarily applied in a weight ratio of from 10:1 to 0.1:1, preferably from 5:1 to 0.2:1, in particular from 3:1 to 0.3:1.

The application rates of the mixtures according to the invention are, depending on the type of desired effect, from 0.01 to 3 kg/ha, preferably from 0.1 to 1.5 kg/ha, in particular from 0.4 to 1.0 kg/ha. The application rates in this case for the compounds I are from 0.01 to 0.5 kg/ha, preferably from 0.05 to 0.5 kg/ha, in particular from 0.05 to 0.2 kg/ha. The application rates for the compounds II are correspondingly from 0.1 to 1.0 kg/ha, preferably from 0.4 to 1.0 kg/ha, in particular from 0.4 to 0.8 kg/ha.

In seed treatment, application rates of mixture of from 0.001 to 50 g/kg of seed, preferably from 0.01 to 10 g/kg, in particular from 0.01 to 8 g/kg, are in general used.

If harmful fungi pathogenic to plants are to be combated, the separate or joint application of the compounds I and II or of the mixtures of the compounds I and II is carried out by spraying or dusting the seeds, the plants or the soils before or after the sowing of the plants or before or after the emergence of the plants.

The fungicidal synergistic mixtures according to the invention or the compounds I and II can be prepared, for example, in the form of directly sprayable solutions, powders and suspensions or in the form of high-percentage, aqueous, oily or other suspensions, dispersions, emulsions, oil dispersions, pastes, dusting compositions, broadcasting compositions or granules and applied by spraying, atomizing, dusting, broadcasting or watering. The application form is dependent on the intended use; in each case it should ensure as fine and uniform a dispersion of the mixture according to the invention as possible.

The formulations are prepared in a manner known per se, eg. by addition of solvents and/or carriers. Inert additives such as emulsifiers or dispersants are customarily admixed to the formulations.

Suitable surface-active substances are the alkali metal, alkaline earth metal or ammonium salts of aromatic sulfonic acids, eg. lignosulfonic, phenolsulfonic, naphthalenesulfonic and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octadecanols or fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ether, ethoxylated isooctyl-, octyl- or nonylphenol, alkylphenol or tributylphenyl polyglycol ethers, alkylaryl polyether alcohols, isotridecyl alcohol, fatty alcohol ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powders, broadcasting and dusting compositions can be prepared by mixing or joint grinding of the compounds I or II or of the mixture of the compounds I and II with a solid carrier.

Granules (eg. coated, impregnated or homogeneous granules) are customarily prepared by binding the active compound or the active compounds to a solid carrier.

Fillers or solid carriers used are, for example, mineral earths such as silica gel, silicic acid, silicates, talc, kaolin, limestone, lime, chalk, bole, loess, clay, dolomite, diatomaceous earth, calcium sulfate and magnesium sulfate, magnesium oxide, ground plastics, and also fertilizers such as ammonium sulfate, ammonium phosphate, ammonium nitrate, ureas and plant products such as cereal flour, tree bark meal, wood meal and nutshell meal, cellulose powder or other solid carriers.

The formulations in general contain from 0.1 to 95% by weight, preferably from 0.5 to 90% by weight, of one of the compounds I or II or of the mixture of the compounds I and II. The active compounds are in this case used in a purity of from 90% to 100%, preferably from 95% to 100% (according to NMR spectrum or HPLC).

The compounds I or II or the mixtures or the corresponding formulations are applied by treating the harmful fungi or the plants, seeds, soils, areas, materials or spaces to be kept free from them with a fungicidally active amount of the mixture, or of the compounds I and II in the case of separate application. Application can be carried out before or after attack by the harmful fungi.

It was possible to determine the synergistic effect of the mixtures according to the invention by the formula of S. R. Colby (Weeds 15, (1967) 20–22)

$$E = X + Y - X \times Y/100$$

the variables having the following meanings:

X is the measurable effect of the active compound I at an application rate [a]

Y is the measurable effect of the active compound II at an application rate [b]

E is the expected measurable effect of a mixture of the active compound I at the application rate [a] and of the active compound II at the application rate [b]

The difference between the expected value E according to Colby and the measured value shows whether synergism (potentiation of the effect or increase in the action) or antagonism (weakening of the effect or reduction in the action) is present, or if both values agree, that only additive effects have an influence.

It was possible to show the improved biological action of the mixtures in comparison with the individual substances by the following tests:

*Puccinia recondita*

Leaves of wheat seedlings (variety "Frühgold") were treated with the aqueous active compound preparation. On the next day the treated plants were dusted with spores of brown rust (*Puccinia recondita*) and the plants treated in this way were incubated for 24 h at 20°–22° C. and a relative atmospheric humidity of 90–95%. After a further 8 days at 20°–22° C. and 65–70% relative atmospheric humidity the extent of fungal development was determined. Evaluation was carried out visually (data on the infected leaves in %).

The potency was calculated according to the formula of Abbott as follows:

Potency=[1−(% attack after treatment)/(% attack without treatment)]×100

The results are compiled in the following tables:

| Active compound | Application rate [ppm] | Potency [Abbott] |
|---|---|---|
| I.A | 500 | 89 |
| I.A | 250 | 78 |
| I.A | 125 | 78 |
| I.A | 100 | 78 |
| I.A | 50 | 67 |
| I.A | 25 | 11 |
| I.A | 12.5 | 22 |
| Pyrimethanil | 500 | 22 |

-continued

| Active compound | Application rate [ppm] | Potency [Abbott] |
|---|---|---|
| Pyrimethanil | 250 | 0 |
| Pyrimethanil | 125 | 0 |
| Pyrimethanil | 100 | 0 |
| Pyrimethanil | 50 | 0 |
| Pyrimethanil | 25 | 0 |
| Pyrimethanil | 12.5 | 0 |
| Mepanipyrim | 500 | 0 |
| Mepanipyrim | 250 | 0 |
| Mepanipyrim | 125 | 0 |
| Mepanipyrim | 100 | 0 |
| Mepanipyrim | 50 | 0 |
| Mepanipyrim | 25 | 0 |
| Mepanipyrim | 12.5 | 0 |

The activities achieved with the mixtures according to the invention are compiled in the following tables:

| I.A [ppm] | Pyrimethanil [ppm] | Potency (observed) | Potency (according to Colby) |
|---|---|---|---|
| 250 | 250 | 94 | 78 |
| 125 | 125 | 94 | 78 |
| 50 | 50 | 89 | 67 |
| 25 | 25 | 83 | 11 |
| 250 | 25 | 89 | 78 |
| 125 | 12.5 | 89 | 78 |
| 50 | 5 | 78 | 67 |
| 25 | 2.5 | 78 | 11 |
| 25 | 250 | 83 | 11 |
| 12.5 | 125 | 78 | 22 |

| I.A [ppm] | Mepanipyrim [ppm] | Potency (observed) | Potency (according to Colby) |
|---|---|---|---|
| 100 | 100 | 83 | 78 |
| 50 | 50 | 78 | 67 |
| 25 | 25 | 67 | 11 |
| 50 | 500 | 78 | 67 |

We claim:
1. A fungicidal mixture containing in synergistic fungicidally effective amounts of:

a) a compound of the formula IB

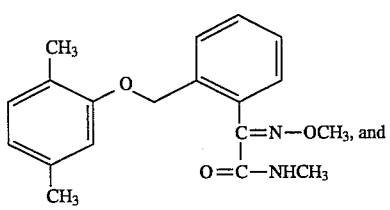

I.B b) a pyrimidine of the formula II

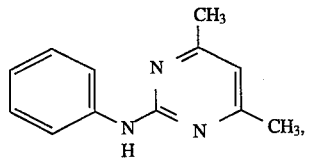

II wherein the weight ratio of the compound IB to the compound II is from 10:1 to 0.1:1.

2. The fungicidal mixture of claim 1, wherein the weight ratio of the compound IB to the compound II is from 5:1 to 0.2:1.

3. The fungicidal mixture as claimed in claim 1, wherein the weight ratio of the compound IB to the compound II is from 3:1 to 0.3:1.

4. A process for combatting harmful fungi, which comprises treating the harmful fungi, their habitat or the plants, seeds, soils, areas, materials or spaces to be kept free from them with from 0.01 to 3 kg/ha of a mixture containing in synergistic fungicidally effective amounts of:

a) a compound of the formula IB

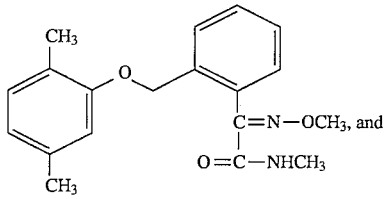

b) a pyrimidine of the formula II

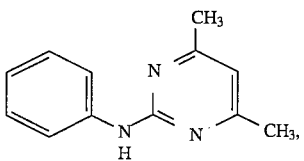

wherein the weight ratio of the compound IB to the compound II is from 10:1 to 0.1:1.

5. The process as claimed in claim 4, wherein the weight ratio of the compound IB to the compound II is from 5:1 to 0.2:1.

6. The process as claimed in claim 4, wherein the weight ratio of the compound IB to the compound II is from 3:1 to 0.3:1.

* * * * *